US006412482B1

(12) United States Patent
Rowe

(10) Patent No.: US 6,412,482 B1
(45) Date of Patent: Jul. 2, 2002

(54) AVALANCHE SURVIVAL PACK ASSEMBLY

(76) Inventor: Carl D. Rowe, 2417 Warwick La., Colorado Springs, CO (US) 80909

( * ) Notice: Subject to any disclaimer, the term of this patent is extended or adjusted under 35 U.S.C. 154(b) by 0 days.

(21) Appl. No.: 09/490,131

(22) Filed: Jan. 24, 2000

(51) Int. Cl.[7] ........................... A61M 16/00; A62B 7/00

(52) U.S. Cl. ........................... 128/204.18; 128/200.24; 128/205.12

(58) Field of Search ........................ 128/204.18, 204.17, 128/201.25, 205.27, 205.22, 205.21, 205.12, 201.23, 202.19, 205.25, 207.18, 202.15, 201.11

(56) References Cited

U.S. PATENT DOCUMENTS

| | | | | | |
|---|---|---|---|---|---|
| 3,227,208 | A | * | 1/1966 | Potter, Jr. et al. | 128/201.21 |
| 3,496,703 | A | * | 2/1970 | MacLeod et al. | 128/204.15 |
| 3,592,157 | A | * | 7/1971 | Schwartz | 116/124 B |
| 3,734,365 | A | * | 5/1973 | Sprecker | 224/8 R |
| 4,114,561 | A | * | 9/1978 | Asaro | 116/124 B |
| 4,295,438 | A | * | 10/1981 | Porter | 116/210 |
| 4,365,628 | A | * | 12/1982 | Hodel | 128/205.12 |
| 4,402,316 | A | * | 9/1983 | Gadberry | 128/201.15 |
| 4,685,456 | A | * | 8/1987 | Smart | 128/204.18 |
| 4,807,614 | A | * | 2/1989 | Van der Smissen et al. | 128/201.23 |
| 4,850,031 | A | * | 7/1989 | Allsop et al. | 455/49 |
| 4,856,508 | A | * | 8/1989 | Tayebi | 128/206.12 |
| 5,105,067 | A | * | 4/1992 | BreBrekkestran et al. | 219/497 |
| 5,203,325 | A | * | 4/1993 | Carr | 128/202.26 |
| 5,400,934 | A | * | 3/1995 | Ducros | 128/202.15 |
| 5,490,501 | A | * | 2/1996 | Crowley | 128/204.17 |
| 5,947,116 | A | * | 9/1999 | Gamow et al. | 128/201.11 |
| 6,000,395 | A | * | 12/1999 | Brown | 128/202.19 |
| 6,167,249 | A | * | 12/2000 | Hereford et al. | 455/404 |

FOREIGN PATENT DOCUMENTS

| | | | | |
|---|---|---|---|---|
| GB | 2185141 A | * | 7/1987 | 128/204.18 |

* cited by examiner

*Primary Examiner*—John G. Weiss
*Assistant Examiner*—Darwin P. Erezo
(74) *Attorney, Agent, or Firm*—Phillip A. Rein

(57) ABSTRACT

The avalanche survival pack assembly includes 1) a main support chest pack assembly to be secured as by a waist support assembly and a shoulder harness assembly to a user thereof; 2) an oxygen supply assembly or means to provide oxygen through a nose/mouth mask assembly to be worn by an avalanche victim and placed in operation on initially observing being caught up within an avalanche condition; 3) an auxiliary power supply assembly to provide electrical battery power to an oxygen conserving assembly or means and a radio signal transmit beacon assembly or means; 4) the radio signal transmit beacon assembly to transmit a radio signal therefrom for aiding in locating the avalanche victim by avalanche rescuers; 5) a visual location indicator assembly having a lengthy, brightly colored ribbon-like material and having one end connected to the main support chest pack assembly and the other end to be trailed outwardly hoping to be exposed on a top surface of the avalanche snow pack; and 6) a control circuit assembly operable to automatically energize itself on closing an "on" switch to provide oxygen to the avalanche victim even though the victim may be in an unconscious condition. The main pack assembly is provided with a CO2 absorbing foam material which is important in increasing the chances of an avalanche victim's survival. The oxygen supply assembly has been modified with an oxygen conserving assembly to provide a pulsating supply of oxygen to the avalanche victim which is sufficient to provide a life-sustaining oxygen condition for a period of at least one hour. The nose/mouth mask assembly is provided with a face mask member having discharge valve members to discharge carbon dioxide from the nose and mouth sections of the avalanche victim and having a teeth grip member to be grasped by teeth of the avalanche victim to securely hold in a usage position.

14 Claims, 4 Drawing Sheets

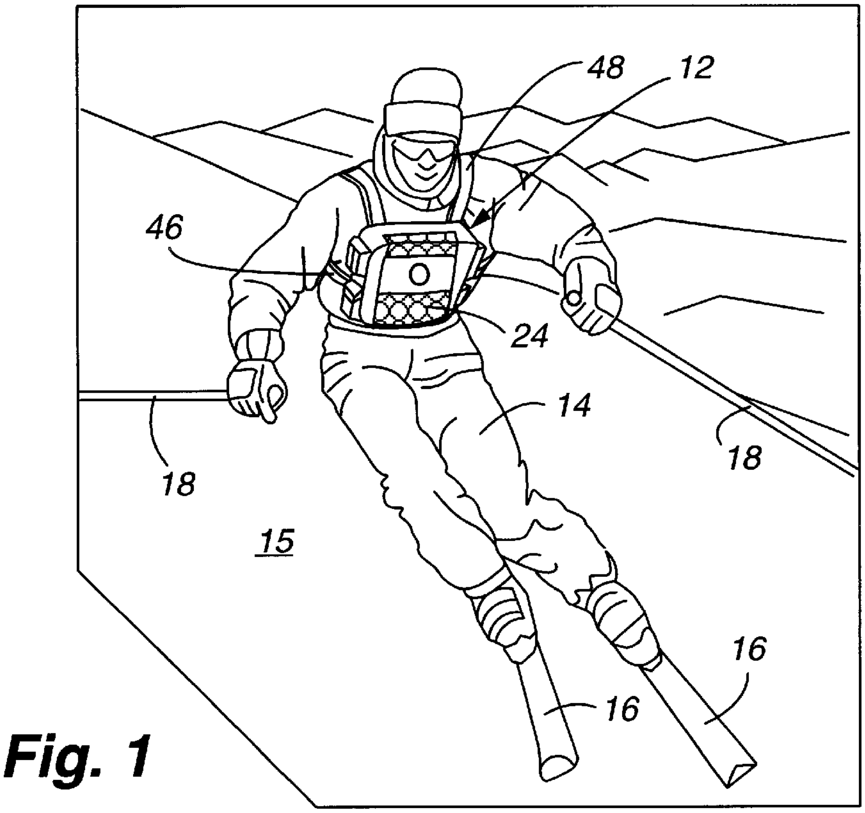
Fig. 1
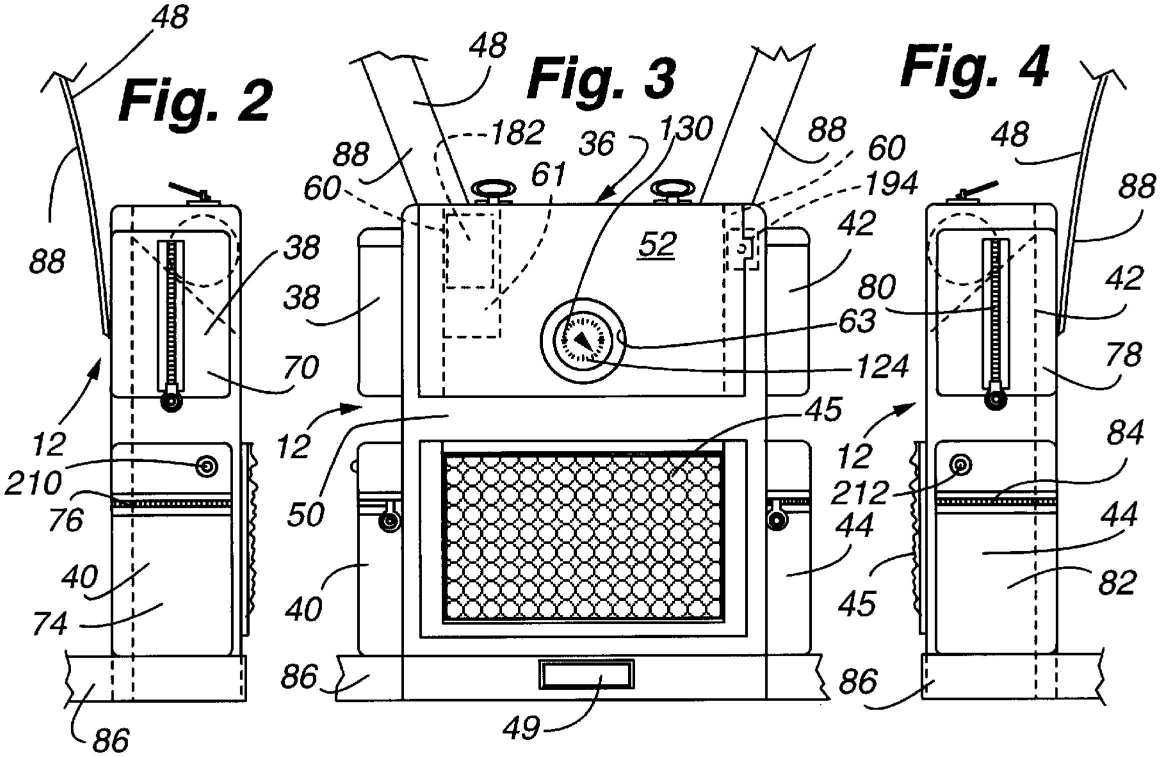
Fig. 2
Fig. 3
Fig. 4

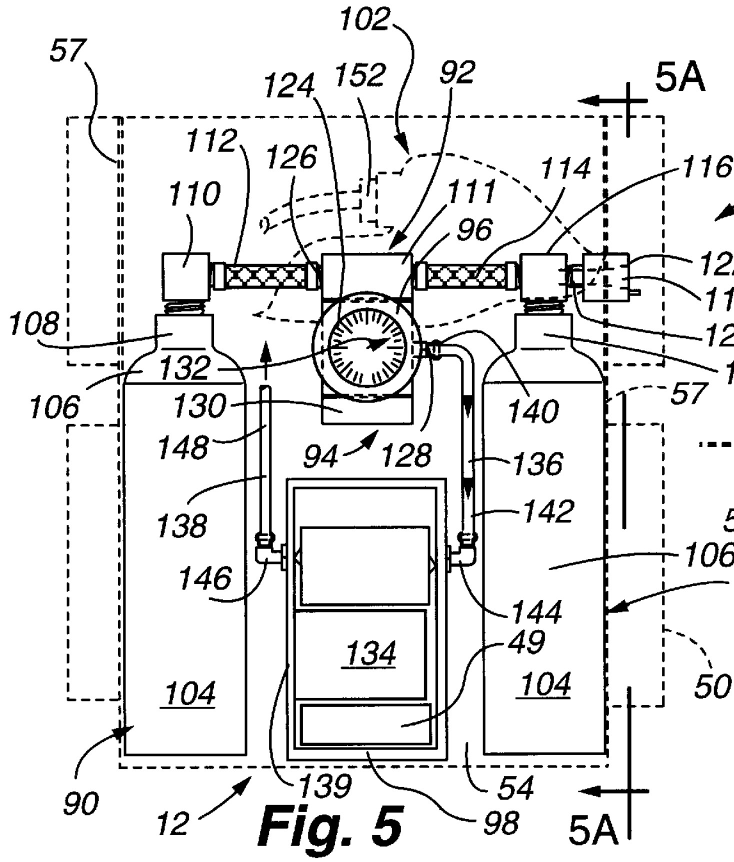
Fig. 5
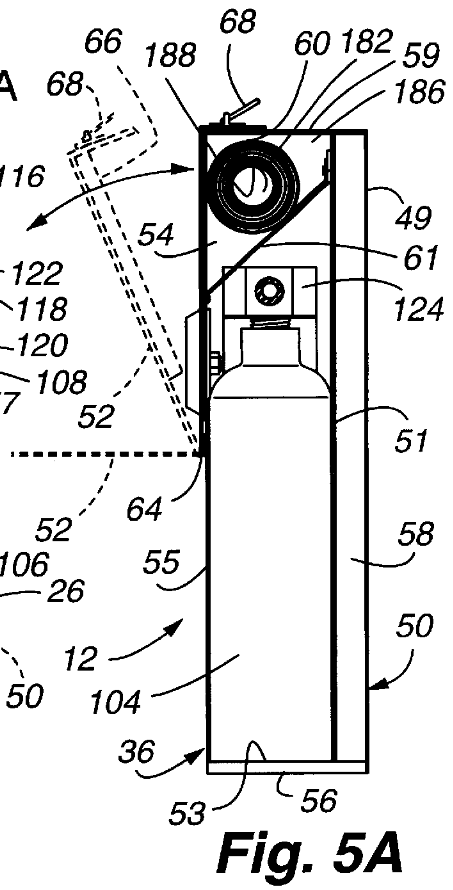
Fig. 5A
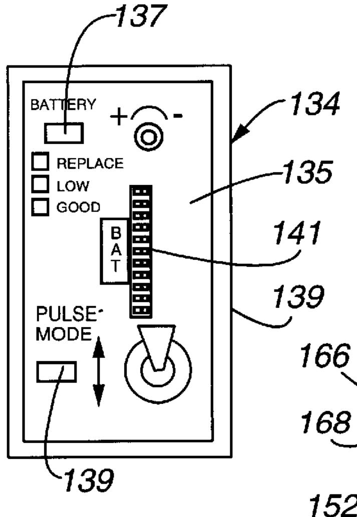
Fig. 6
Fig. 7
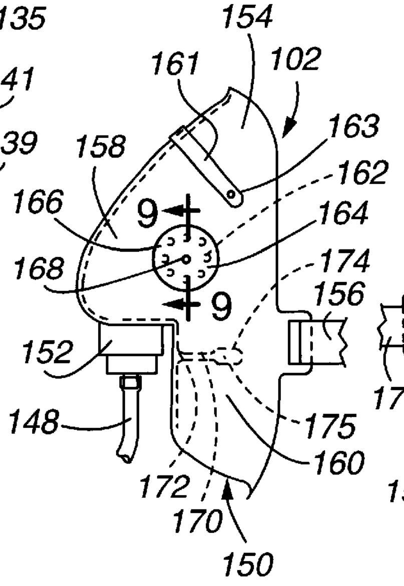
Fig. 8
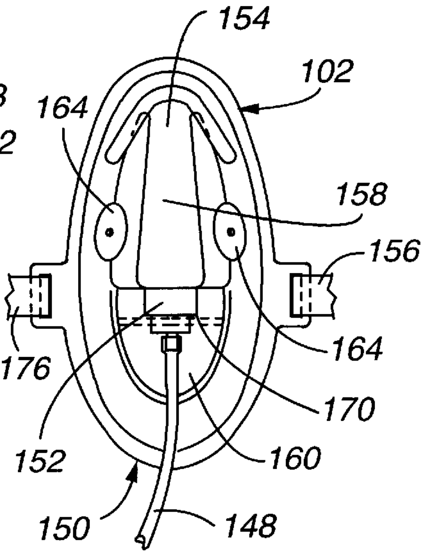

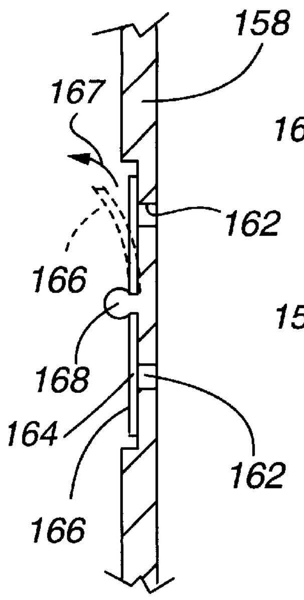
Fig. 9
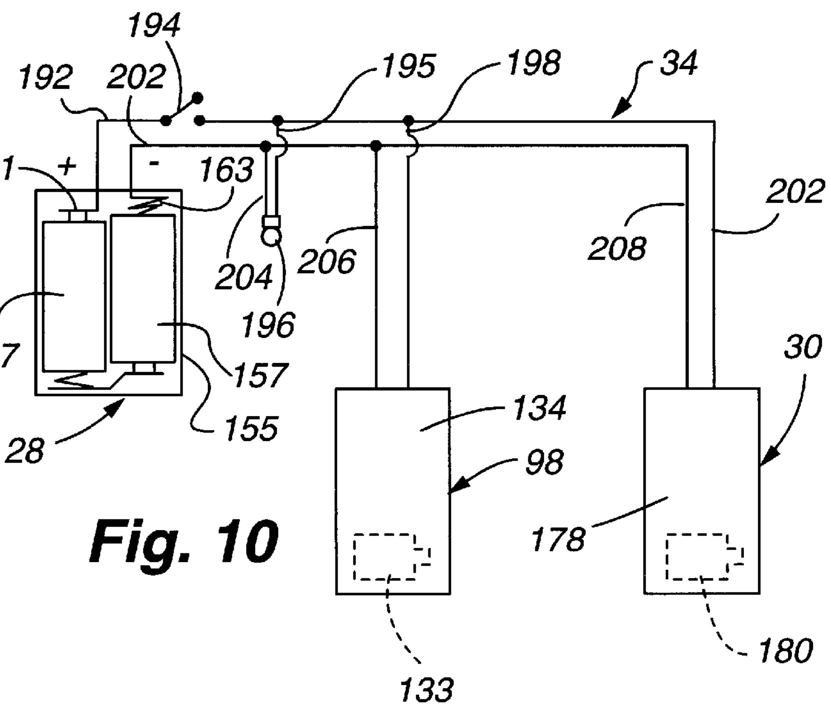
Fig. 10
Fig. 11
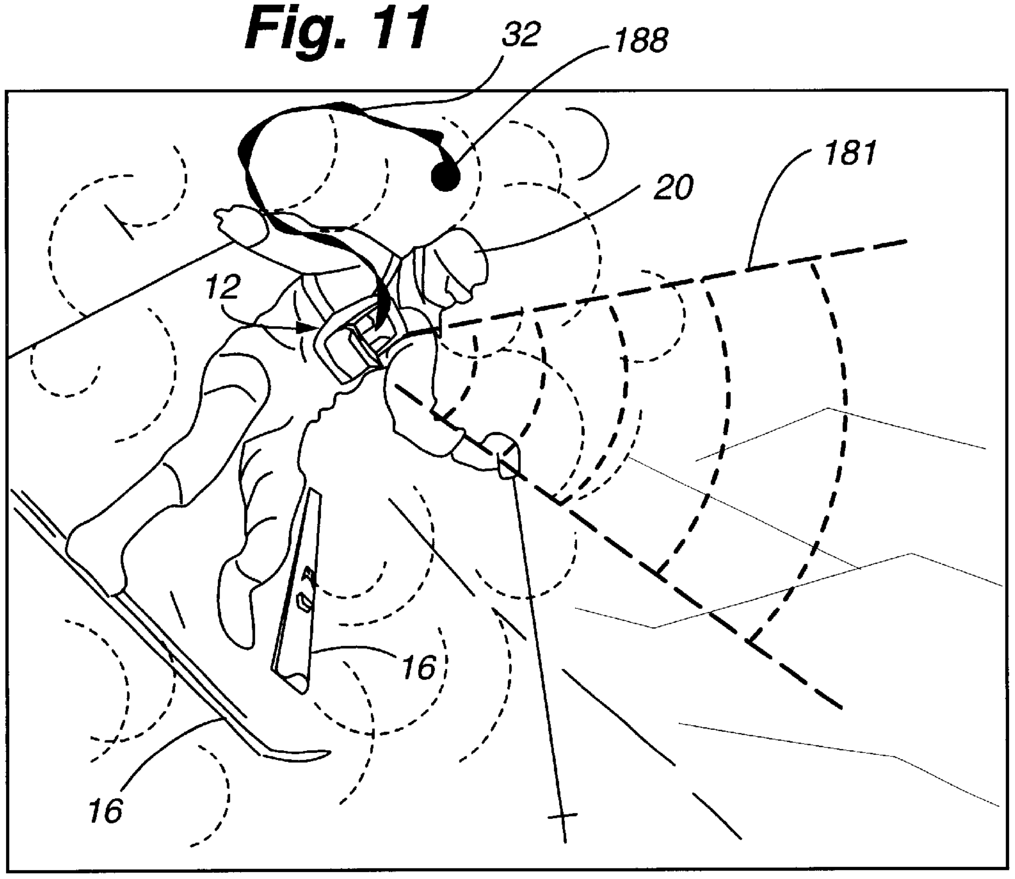

AVALANCHE SURVIVAL PACK ASSEMBLY

PRIOR ART

The inventor has conducted a patent search on the above identified invention and has located the following United States patents:

| U.S. Pat. No. | Invention | Inventor |
|---|---|---|
| 4,114,561 | AVALANCHE RESCUE MARKER SYSTEM | Vito F. Asaro |
| 4,365,628 | AVALANCHE SURVIVAL VEST | Carl F. Hodel |
| 4,850,031 | AVALANCHE VICTIM LOCATING APPARATUS | Allsop et al. |

The Asaro patent discloses an avalanche rescue marker system which utilizes a balloon attached by a brightly colored tether to a jacket worn by an avalanche victim. The balloon is operable to be filled with lighter-than-air material, such as helium, so, hopefully, it will float above avalanche snow and debris to clearly locate the victim buried by the subject avalanche.

The Hodel patent discloses an avalanche survival vest to be worn around the chest by skiers and mountaineers and operable to provide oxygen to breathe and to serve as a flotation device to help victims survive if caught in an avalanche. The Hodel patent also discloses that the vest has a CO2 absorber chamber, a mouthpiece breathing hose, and a compressed oxygen cartridge which can be released instantly by biting hard on the mouthpiece hose or pushing a button on the mouthpiece hose.

The Allsop et al patent discloses an avalanche victim locating apparatus and is mainly a special type of transmitter beacon signal plus an alarm device to be heard by avalanche rescuers. There are numerous types of transmitter beacons known in the prior art as will be discussed.

BACKGROUND OF THE INVENTION

There are some 2000 reported avalanches in the State of Colorado each season (many times they are not reported).

In Switzerland alone, an average of 100 persons die in avalanches each year. As many as 150 to 200 per year for the entire Alpine Region. In the United States, an average of 20 persons per year die in avalanches (approximately 12 per year in Colorado).

Persons killed by avalanches, as reported to one organization, the CSAC, for the year 1995 through Jan. 19, 1999.

| | USA/Canada | Other Countries | Total |
|---|---|---|---|
| 1998–1999 | 21 (3 mo. period) | 38 | 57 |
| 1997–1998 | 50 | 254 | 304 |
| 1996–1997 | 46 | 156 | 202 |
| 1995–1996 | 34 | 43 | 77 |
| TOTAL | 151 | 491 | 642 |
| AVERAGE | 38/Year | 123/Year | 160/Year |

These statistics DO NOT include the countries of Austria, Italy, Germany, or Japan (and a few other minor countries).

If we include the fatality estimates for these countries, as stated in "The Avalanche Book", a respected and authoritative work on the subject of avalanches, then the world-wide total would go to 742 fatalities for that period.

These fatalities occurred in just the last 4 seasons with today's best available technology.

By far, most victims who are equipped with radio beacons are found and rescued. Many are not, or are found too late. By far, most avalanches victims die of suffocation from snow burial within the first 30 minutes or less.

The applicant's concept is to provide a compact, lightweight chest pack which is small enough and lightweight enough that it will not restrict, in any way, free movement of a skier or other user, and will contain everything necessary for avalanche survival (assuming there are no serious physical injuries).

In the event of an avalanche, an avalanche survival pack assembly of this invention would be instantly activated within just a few seconds. All of the components of this invention are fully automatic and actuated by one simple action on the part of the skier or other user by simply opening a closure flap assembly on a main support chest pack assembly.

The key elements of a successful rescue of an avalanche victim consist of 1) locating the avalanche victim quickly; and 2) enabling the avalanche victim buried under avalanche snow and debris to breathe for a longer period of time, up to 60 minutes, greatly enhancing chances of survival.

The avalanche survival pack assembly provides two ways to aid in the avalanche victim being located as follows:

1) providing a radio beacon with "Receive" and "Transmit" modes and the beacon is automatically switched to "Transmit" mode in case the avalanche victim forgot to do so ahead of time which can be accomplished mechanically or electronically; and
2) having a 50 foot long×1" wide brightly colored nylon ribbon member which is coiled up and attached to the main support chest pack assembly on one end and falls out by gravity upon the avalanche victim opening the closure flap assembly.

The ribbon, which may be of fluorescent orange color, is allowed to "float free" as the avalanche victim is being carried down the slope. Portions of the orange ribbon member should be visible above the surface of the snow, enabling rescuers to locate the avalanche victim.

The avalanche survival pack assembly provides three ways to keep victims alive until rescued, as follows:

1) a mask assembly covers a nose, mouth and chin area of the avalanche victim which keeps the air passages open and free from snow while allowing the avalanche victim to breathe;
2) an automatic, oxygen breathing system comprised of a pair of small, lightweight, high pressure mini-oxygen cylinders connected to a pressure regulator assembly which reduces the pressure down to 20 PSI; and low pressure oxygen is connected to an automatic oxygen conserving assembly which releases small, metered bursts of 95% pure oxygen to the avalanche victim through the nose/mouth mask assembly; and
3) the avalanche survival pack assembly contains a ½" thick foam padded area, next to the user's chest area, which will a) provide for chest cavity expansion; and b) contain a material that will absorb CO2.

PREFERRED EMBODIMENT OF THE INVENTION

In one preferred embodiment of this invention, an avalanche survival pack assembly is operable to be supported on the waist, shoulder, and chest area of a skier or other user who is normally in a ski area having a great possibility of avalanche danger due to unstable snow conditions. The skier normally is traversing the snow on skis and having ski poles to aid in movement.

The avalanche survival pack assembly is operable to provide means to increase a chance of survival when the skier or other user suddenly becomes an avalanche victim and may be covered with several inches or feet of snow. A rescue effort needs to be convened immediately as the possibility of survival of the avalanche victim decreases rapidly in a short period of time.

The avalanche survival pack assembly includes 1) a main support chest pack assembly or means; 2) an oxygen supply assembly or means mounted within the main support chest pack assembly; 3) an auxiliary power supply assembly mounted within the main support chest pack assembly; 4) a radio signal transmit beacon assembly mounted within the main support chest pack assembly and operable to transmit an emergency radio signal; 5) a visual location indicator assembly mounted within the main support chest pack assembly and operable to dispense and trail a visual ribbon member when automatically released from the main support chest pack assembly; and 6) a control circuit assembly operably connected from an auxiliary power supply assembly, to the radio signal transmit beacon assembly, and the oxygen supply assembly to provide a sufficient auxiliary power supply.

The main support chest pack assembly includes 1) a main pack assembly; 2) an accessory pocket assembly; 3) a battery pack pocket assembly; 4) a filler valve pocket assembly; 5) a radio beacon pocket assembly; 6) a waist support assembly for securing about a waist area of a user thereof; and 7) a shoulder harness assembly adapted to be placed about a shoulder area of the user thereof for vertical support.

The main pack assembly includes 1) a main pack member; and 2) a closure flap assembly. The main pack member has a pack container cavity defined by a back wall, an intermediate wall, a bottom wall, a front wall, opposed side walls, and a top wall.

Further, the main pack member includes 1) a bottom support member; 2) a CO2 absorbing foam member; 3) Velcro connector hook members for attachment to the closure flap assembly; and 4) a ribbon support strap.

The closure flap assembly includes 1) a main closure flap member pivotally connected by a closure hinge member to the front wall of the main pack member; 2) Velcro connector loop members engageable with Velcro connector hook members on the main pack member so as to hold in a closed condition; and 3) detach pull ring members mounted on a top surface of the closure flap member operable to be pulled forwardly of the users chest area to disconnect the Velcro connector hook members from the Velcro connector loop members when in an “activated” condition as will be explained.

The waist support assembly includes a support strap member to be placed about a waist area of a skier or other user and having a snap lock belt buckle member to secure the support strap member about the waist area.

The shoulder harness assembly includes a pair of spaced shoulder strap members placed about the shoulder area of the user and having thereon respective snap lock strap buckle members to hold in a secure adjusted position.

The oxygen supply assembly includes 1) an oxygen supply reservoir assembly; 2) a cylinder connector assembly interconnecting a pair of high pressure oxygen cylinder members in the oxygen supply reservoir assembly; 3) a pressure regulator assembly connected to the cylinder connector assembly to regulate a usage pressure of oxygen to be utilized by an avalanche victim; 4) a pressure gauge assembly connected to the pressure regulator assembly to visually indicate the pressure of oxygen being dispensed therefrom; 5) an oxygen conserving assembly to receive oxygen from the pressure regulator assembly operable to extend time of obtaining life-sustaining oxygen from the oxygen cylinder members; and 6) a nose/mouth mask assembly for receiving the oxygen being dispensed from the oxygen conserving assembly and to supply same to the avalanche victim in a manner to be explained.

The oxygen supply reservoir assembly includes a pair of oxygen cylinder members, each having a main body member and a threaded discharge opening at an upper end thereof. These oxygen cylinder members are adapted to contain highly pressurized gas, such as oxygen, of 3,000 PSI so as to maintain a one hour supply of oxygen to the avalanche victim in a manner to be explained.

The cylinder connector assembly connects each oxygen cylinder member to the pressure regulator assembly.

The pressure regulator assembly includes a discharge opening which is to be connected to the oxygen conserving assembly to supply 20 PSI oxygen thereto.

The pressure gauge assembly includes a pressure gauge member having a pressure indicator dial to indicate the pressure that is being discharged to the oxygen conserving assembly.

The oxygen conserving assembly includes 1) an oxygen conserving member; 2) an oxygen inlet hose assembly; 3) an oxygen outlet hose assembly; and 4) a battery member to provide a power supply to the oxygen conserving member.

The oxygen conserving member is available in the prior art operable to supply a controlled amount of oxygen to prolong the time of supplying life-sustaining oxygen from the oxygen cylinder members to the avalanche victim.

The oxygen inlet hose assembly includes 1) an outlet hose fitting connected to the pressure regulator assembly; 2) an outlet hose member having one end connected to the outlet hose fitting; and 3) a device inlet fitting connected to an outlet end of the outlet hose member and to oxygen conserving assembly.

The oxygen outlet assembly includes a device outlet fitting connected to the oxygen conserving member and having connected thereto an outlet hose member. An outer end of the outlet hose member is connected to the nose/mouth mask assembly.

As best noted in FIGS. 7 and 8, the nose/mouth mask assembly includes a face mask assembly which is connected by a mask inlet fitting to the outlet hose member of the oxygen outlet hose assembly of the oxygen conserving assembly.

The face mask assembly includes face mask member which is secured by a strong elastic anchor strap assembly about a head area of an avalanche victim in a manner to be explained.

The face mask member includes 1) a main nose section; 2) a main mouth section integral with the main nose section; and 3) a nose strap member made of a bendable metallic material to achieve more custom fitting around a nose area of an avalanche victim.

The main nose section has 1) a plurality of air discharge openings in a circle on opposite side walls and 2) a discharge valve member associated with each opposed groupings of the air discharge openings.

The discharge valve members are a plastic valve member secured as by respective anchor members so as to cover the respective grouping of air discharge openings to act as a flapper one-way valve to allow discharge air from the avalanche victim to exit the face mask member.

The main mouth section includes a teeth grip member having one anchor end secured to an inner portion of the main mouth section and an outer bite section to be clamped by an avalanche victim to hold the entire face mask member in an adjacent usage condition as will be explained.

The nose strap member is made of a bendable metal material secured to the main nose section as by anchor members.

The nose strap member can be bent by an avalanche victim's fingers to achieve a desired seal about the avalanche victim's nose area which, in conjunction with the anchor strap assembly, achieves a sealing of the face mask member to the avalanche victim's face area about the nose and mouth area.

The auxiliary power supply assembly includes a battery back housing having a pair of battery members therein. The battery members are interconnected in series, each having a positive pole and a negative pole.

The auxiliary power supply assembly is to provide an additional supply of electrical energy, being a 3.0 volt power supply, to assure that the radio signal transmit beacon assembly and the oxygen supply assembly are operable to be continuously energized for up to at least one hour while supplying oxygen to an avalanche victim.

The radio signal transmit beacon assembly is known in the prior art and includes an avalanche rescue beacon member energized by a beacon battery member and transmitting a radio signal in all directions in hopes that avalanche rescuers will find the avalanche victim in the shortest time period due to receiving the transmitted radio signals on a receiver member held by the respective avalanche rescuers.

The visual location indicator assembly includes a coiled ribbon member supported within the main pack assembly and one end thereof, being an anchor end, is secured to the intermediate wall of the main pack member and a free end trails the avalanche victim when in a condition of an uncoiled ribbon member.

The coiled ribbon member has the free end which, when the closure flap assembly is pulled outwardly to the emergency usage condition, the free end is allowed to flow outwardly therefrom and, hopefully, would be visible to the avalanche rescuers on top of the snow and debris created by the avalanche.

During emergency usage, the uncoiled ribbon member has thereon a direction indicia with an arrow indicia so that when observed by the avalanche rescuers, the arrow indicia would point in the direction of the avalanche victim. This is very important so that the avalanche rescuers are not proceeding in the wrong direction in case the free end is buried within the snow and debris created by the avalanche.

The control circuit assembly utilizes the respective battery members in the radio signal transmit beacon assembly and the oxygen supply assembly with the auxiliary power supply assembly to assure that sufficient electrical energy is available to filly energize the electrical elements for a period of at least one hour or more.

A light assembly is provided in the main support chest pack assembly with a light bulb therein on the outer front portion of the main pack assembly so as to provide light therein to add comfort to the avalanche victim. This light bulb is automatically energized when the enclosure flap assembly is pulled downwardly to the activated condition which also automatically energizes the radio signal transmit beacon assembly and the oxygen supply assembly. These are automatically energized once the closure flap assembly has been pulled even if the avalanche victim has been knocked unconscious during tumbling down a hill with the avalanche snow and debris.

OBJECTS OF THE INVENTION

One object of this invention is to provide an avalanche survival pack assembly to be worn on a chest area of a downhill or cross country skier or other user when in an avalanche area and providing means thereon for survival with an oxygen supply reservoir assembly connected through an oxygen conserving assembly to provide oxygen supplied through a nose/mouth mask assembly to the avalanche victim for at least a one hour period.

Another object of this invention is to provide an avalanche survival pack assembly including a main support chest pack assembly to be worn on a person's chest area and being able to 1) supply oxygen through a nose/mouth mask assembly for a period of one hour or more; 2) transmit radio signals through a radio signal transmit beacon assembly which can be received by avalanche rescuers; and 3) provide a visual location indicator assembly having a ribbon member that will be trailed out from the avalanche victim and, hopefully, a portion thereof will be visible on a top layer of the avalanche snow pack for the rescuers to find and locate the avalanche victim.

One other object of this invention is to provide an avalanche survival pack assembly having a main support chest pack assembly operable to receive and support thereon 1) an oxygen supply assembly; 2) an auxiliary power supply assembly; 3) a radio signal transmit beacon assembly to transmit radio signals therefrom; and 4) a visual location indicator assembly operable to trail a brightly colored ribbon member behind the avalanche victim while being tumbled down the avalanche occurring mountain in hopes of providing a visual indicator as to the location of the avalanche victim.

A further object of this invention is to provide an avalanche survival pack assembly including a main support chest pack assembly to receive and support numerous items therein necessary to survive while being buried under an avalanche snow pack and having therein an oxygen supply assembly having an oxygen supply reservoir assembly with oxygen cylinder members connected to a pressure regulator assembly and an oxygen conserving assembly to provide a pulsating and predetermined amount of oxygen to a nose/mouth mask assembly to be worn about the avalanche victim's face area to provide a supply of life sustaining oxygen to the avalanche victim for a period of one hour or longer.

One further object of this invention is to provide an avalanche survival pack assembly having numerous elements conveyed by a main support chest pack assembly to be worn against a user's chest area and supported by a shoulder harness assembly and a waist support assembly and having therein 1) an oxygen supply means to provide oxygen to the avalanche victim through a nose/mouth mask assembly; 2) being automatically operable to energize an auxiliary power supply assembly to supply power through a controlled circuit assembly to a radio signal transmit beacon assembly, a light member, and an oxygen conserving assembly and 3) automatically operable to release a visual location indicator assembly, being an elongated brightly colored ribbon member, having arrow indicia thereon hoping that at least a portion of the ribbon member will be visible on top of the packed avalanche snow for the avalanche rescuers to find and quickly evacuate the avalanche victim from being buried in the snow environment.

Still, one other object of this invention is to provide an avalanche survival pack assembly which is readily carried against a chest area of a user thereof; being lightweight; substantially maintenance free; sturdy in construction; economical to manufacture; reliable in operation so as to automatically energize a radio signal transmit beacon assembly and an oxygen supply assembly; automatically dispensing a visual location indicator assembly when the user finds itself in a path of an avalanche and possibly being buried and subject to possible suffocation and hypothermia within a dense snow pack.

Various other objects, advantages, and features of the invention will become apparent to those skilled in the art from the following discussion, taken in conjunction with the accompanying drawings, in which:

FIGURES OF THE INVENTION

FIG. 1 is a respective view of a cross country or downhill skier in a ski area utilizing skis and ski poles and, having mounted against a front chest of the user an avalanche survival pack assembly of this invention;

FIG. 2 is a fragmentary side elevational view of one side of the avalanche survival pack assembly of this invention;

FIG. 3 is a fragmentary front elevational view of the avalanche survival pack assembly of this invention;

FIG. 4 is a fragmentary side elevational view of the other side of the avalanche survivial pack assembly of this invention;

FIG. 5 is a front elevational view of the avalanche survival pack assembly of this invention with a main support chest pack assembly illustrated in dotted lines;

FIG. 5A is a sectional view taken along line 5A—5A in FIG. 5;

FIG. 6 is a top plan view of an oxygen conserving assembly of this invention;

FIG. 7 is a fragmentary side elevational view of a nose/mouth mask assembly of this invention;

FIG. 8 is a fragmentary front elevational view of the nose/mouth mask assembly of this invention;

FIG. 9 is an enlarged fragmentary sectional view taken along line 9—9 in FIG. 7;

FIG. 10 is an electrical schematic diagram;

FIG. 11 is a perspective view illustrating the cross country or downhill skier coming into contact or preparing to be contacted by rumbling snow in an avalanche approaching condition and having a portion of the avalanche survival pack assembly being activated to dispense a visual indication indicator assembly and transmit a radio signal from a radio signal transmit beacon assembly;

Figure 12:
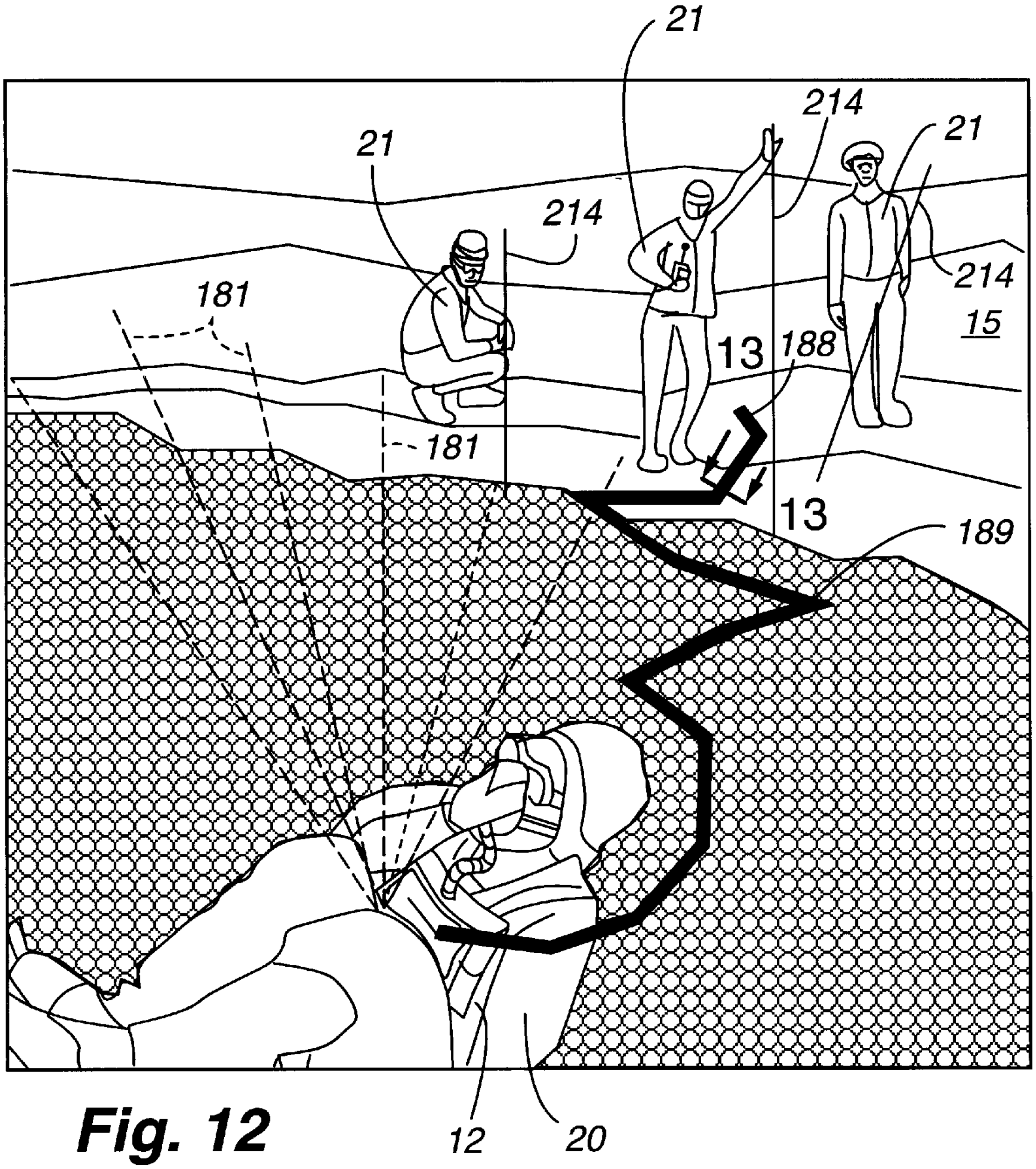
Figure 13:
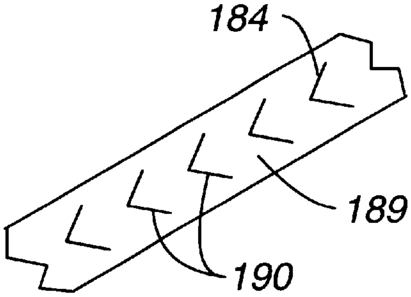

FIG. 12 is view illustrating an avalanche victim as buried within an avalanche snow pack and having 1) the avalanche survival pack assembly which is transmitting a radio signal from the radio signal transmit beacon assembly; 2) the oxygen supply assembly providing oxygen to the nose and mouth area of the avalanche victim through a nose/mouth mask assembly; and 3) indicating a trailing portion of a visual location indicator assembly with a portion thereof revealed on a top surface of the tumbled avalanche snow pack and being observed by avalanche rescuers; and FIG. 13 is a fragmentary sectional view taken along line 13—13 in FIG. 12 and illustrating arrow indicia on an uncoiled ribbon member pointing in a direction in which the avalanche victim may be buried.

The following is a discussion and description of preferred specific embodiments of the avalanche survival pack assembly of this invention, such being made with reference to the drawings, whereupon the same reference numerals are used to indicate the same or similar parts and/or structure. It is to be understood that such discussion and description is not to unduly limit the scope of the invention.

DESCRIPTION OF THE INVENTION

On referring to the drawings in detail, and in particular to FIG. 1, an avalanche survival pack assembly of this invention, indicated generally at 12, is shown as mounted against a front chest area of a cross country or downhill skier 14 and illustrated in a ski area 15 which may be under an avalanche alert. The cross country or downhill skier 14 has a pair of skis 16 thereon and utilizing a ski pole 18 held in each hand in a conventional downhill sking operation.

The avalanche survival pack assembly 12 includes 1) a main support chest pack assembly or means 24; 2) an oxygen supply assembly or means 26; 3) an auxiliary power supply assembly 28; 4) a radio signal transmit beacon assembly 30; 5) a visual location indicator assembly 32; and 6) a control circuit assembly 34 used to provide electrical energy from the auxiliary power supply assembly 28 to the radio signal transmit beacon assembly 30 and a portion of the oxygen supply assembly or means 26, namely, an oxygen conserving assembly 98 as will be explained.

The main support chest pack assembly 24 includes 1) a main pack assembly 36; 2) a waist support assembly 46 to support the main pack assembly 36 about a waist area of the cross country or downhill skier 14; and 3) a shoulder harness assembly 48 adapted to be mounted about a shoulder area of a cross country or downhill skier 14 to provide substantial support in holding the main pack assembly 36 against the chest area of the cross country or downhill skier 14.

The main pack assembly 36 includes a main pack member 50 having a closure flap assembly 52 connected thereto and further including 1) an accessories pocket assembly 38; 2) a battery pack pocket assembly 40; 3) a filler valve pocket assembly 42; 4) a radio beacon pocket assembly 44; and 5) a mesh pocket 45 connected to a lower outer front portion of the main pack member 50.

As noted in FIG. 5A, the main pack member 50 defines therein a pack container cavity 54 having a back wall 49; an intermediate wall 51; a bottom wall 53; a front wall 55; opposed side walls 57; and a top wall 59.

The main pack member 50 includes 1) a bottom support member 56 of a rigid construction; and 2) a CO2 absorbing foam member 58 mounted between the intermediate wall 51 and the back wall 49 being operable to receive and absorb carbon dioxide therein by various types of filter media as will be explained.

Further, the main pack member 50 includes Velcro connector hook members 60 mounted on opposite sides of the front wall 55 and a ribbon support strap 61 secured to the intermediate wall 51 and inclined to the front wall 55 and supporting the visual location indicator assembly 32 as will be explained.

The closure flap assembly 52 includes a closure flap member 62 attached as by a closure hinge member 64 to a mid portion of the front wall 55 of the main pack member 50. The closure flap member 62 is provided with a pressure gauge opening 63 for reasons to be explained.

The closure flap assembly 52, on opposite inner vertical sides thereof, is provided with Velcro connector loop members 66 which are engageable with the Velcro connector hook members 60 on the main pack member 50 to hold in the enclosed condition as shown in FIG. 3.

Further, the closure flap assembly 52 is provided with a pair of spaced detach pull ring members 68 mounted on an upper outer surface of the closure flap member 62. The detach pull ring members 68 are to be pulled forwardly to pivot the closure flap member 62 about the closure hinge member 64 when in an emergency activated condition as will be explained.

The accessories pocket assembly 38 includes an accessories pocket member 70 to hold various items therein such as sun screen, sun glasses, etc. and being enclosed by a vertically extended accessories closure zipper member 72.

The battery pack pocket assembly 40 includes a battery pocket member 74 to receive the auxiliary power supply assembly 28 therein and enclosed by a horizontally extended battery closure zipper member 76.

The filler valve pocket assembly 42 is to enclose a filler valve member therein and is formed with a valve pocket member 78 being selectively enclosed and sealed by a vertically extended valve closure zipper member 80.

The radio beacon pocket assembly 44 is operable to receive and enclose the radio signal transmit beacon assembly 30 and includes a beacon pocket member 82 being selectively enclosed by a horizontally extended beacon closure zipper member 84.

The waist support assembly 46 includes a support belt member 86 which is wrapped around the waist area of the cross country or downhill skier 14 and being secured in the usage condition by a snap lock strap buckle member (not shown).

The shoulder harness assembly 48 includes a pair of spaced parallel shoulder strap members 88, each secured in the attached clamped position about the shoulder area of the cross country or downhill skier 14 as by a snap lock strap buckle member (not shown) on each shoulder strap member 88.

On referring to FIG. 5, the oxygen supply assembly or means 26 includes 1) an oxygen supply reservoir assembly 90; 2) a cylinder connector assembly 92; 3) a pressure regulator assembly 94; 4) a pressure gauge assembly 96; 5) an oxygen conserving assembly 98; and 6) a nose/mouth mask assembly 102 to receive the oxygen in a regulated amount from the oxygen conserving assembly 98 which will be explained.

As noted in FIG. 5, the oxygen supply reservoir assembly 90 includes a pair of high pressure oxygen cylinder members 104, each having a main body 106 and a top female threaded discharge opening 108.

As shown in FIG. 5, the left or first oxygen cylinder member 104 is interconnected by the cylinder connector assembly 92 to the other, or second, oxygen cylinder member 104.

More particularly, the cylinder connector assembly 92 has an elbow member 110 mounted within the threaded discharge opening 108 of the first oxygen cylinder member 104 and connected by a first hose member 112 to the pressure regulator assembly 94 through a first T-connector member 111.

An inner end of the first hose member 112 is connected to the first T-connector member 111 which is connected by a second hose member 114 to a second T-connector member 116.

Further, the cylinder connector assembly 92 includes a quick disconnect member 118 connected to an outer side of the second T-connector member 116 which is used to recharge the oxygen cylinder member 104.

The quick disconnect member 118 has a fitting section 120 connected to a receiving section 122. The receiving section 122 is to receive oxygen during a refilling operation to recharge the oxygen cylinder members 104 to a fully charged condition after use thereof.

The pressure regulator assembly 94 is adapted to receive oxygen under high pressure, such as 3000 PSI, from both of the oxygen cylinder members 104 and then feeding low pressure oxygen at 20 PSI to the oxygen conserving assembly 98 to the pressure regulator assembly 94.

The pressure regulator assembly 94 includes a pressure regulator member 124 having an entrance opening 126 and a discharge opening 128.

The pressure regulator member 124 is well known in the art and operable to take a high pressure source and deliver a low pressure output to the oxygen conserving assembly 98 as will be explained.

The pressure gauge assembly 96 includes a pressure gauge member 130 having a pressure indicator dial 132 thereon. Pressure gauge members 130 are well known in the prior art and assures that a proper adjusted low pressure is being supplied to the oxygen conserving assembly 98.

The oxygen conserving assembly 98 includes 1) an oxygen conserving member 134; 2) an oxygen inlet hose assembly 136 connected between the pressure regulator assembly 94 and the oxygen conserving member 134; 3) an oxygen outlet hose assembly 138 interconnected between the oxygen conserving member 134 and the nose/mouth mask assembly 102; and 4) an oxygen battery member 133 to provide an independent power supply in conjunction with the auxiliary power supply assembly 28 as will be explained.

The oxygen conserving member 134 is well known in the prior art and includes a conserving housing member 139 and a control indicator panel 135.

The oxygen inlet hose assembly 136 includes 1) an outlet hose fitting 140 operable to receive regulated low pressure oxygen from the pressure regulator assembly 94; 2) an outlet hose member 142 having an inlet end connected to the outlet hose fitting 140; and 3) a device inlet fitting 144 connected to the other end of the outlet hose member 142 and to the oxygen conserving member 134.

The oxygen outlet hose assembly 138 has 1) a device outlet fitting 146 connected to the oxygen outlet portion of the oxygen conserving member 134; and 2) an outlet hose member 148 connected to receive oxygen from the device outlet fitting 146 and having an upper outer end thereof connected to the nose/mouth mask assembly 102 for use and operation as will be explained.

The control indicator panel 135 includes 1) a low battery indicator 137; 2) an oxygen dose indicator 139; and 3) a pulse mode indicator 141.

The oxygen conserving member 134 is known in the prior art and is utilized to provide the necessary amount of oxygen to an avalanche victim 20 so that the oxygen supply reservoir assembly 90 will apply pre-adjusted regulated bursts of 95% pure oxygen to the avalanche victim 20 so that the oxygen can be supplied for a period of one hour or longer.

As best shown in FIGS. 7 and 8, the nose/mouth mask assembly 102 includes a face mask assembly 150 having thereon a mask inlet fitting 152 adapted to be connected and receive oxygen from the outer end of the outlet hose member 148.

The face mask assembly 150 includes a main face mask member 154 having a high strength elastic anchor strap assembly 156 connected thereto and operable to be placed about a back surface of a head of the avalanche victim 20 to securely clamp the face mask member 154 about the nose, mouth, and chin area of the avalanche victim 20.

The face mask member 154 includes a main nose section 158 integral with a main mouth section 160 and having an adjustment feature through a nose strap member 161 as will be explained.

The main nose section 158 has a grouping in a circular form of a plurality of discharge openings 162 on each side of the nose area and having a respective discharge valve member 164 cooperating with each of the two opposed groupings of the air discharge openings 162.

As shown in FIG. 9, each discharge valve member 164 includes a one-way valve member 166 secured as by an anchor member 168 in a center of the circular groupings of each set of the air discharge openings 162. The air discharge openings 162 are covered by the respective discharge valve member 164.

The one-way valve member 166 is constructed of a thin flexible plastic material whereupon, the avalanche victim 20 on breathing exhaust air, would move the respective one-way valve member 166 outwardly as shown in dotted lines and by an arrow 167 to achieve discharge therefrom on the discharge of air from the avalanche victim 20.

The main mouth section 160 is to be placed over the chin and mouth area of the avalanche victim 20 and having therein a teeth grip member 170. The teeth grip member 170 has an anchor end 172 and a bite section 174 extended over the main mouth section 160.

The bite section 174 is of a substantial width having an enlarged end portion 175 and operable to be inserted in the mouth area of the avalanche victim 20 and to be clamped by the teeth of the avalanche victim 20. The clamping firmly holds the face mask member 154 in a sealed condition about the mouth and chin area of the avalanche victim 20 so that all of the oxygen is transferred and utilized by the avalanche victim 20 and will not escape therefrom about the face mask member 154.

As shown in FIG. 7, the nose strap member 161 is of a flexible metal material and having opposite ends thereof secured as by anchor members 163 over the crown of the main nose section 158.

The nose strap member 161 can be grasped by the fingers of the avalanche victim 20 and made to bend to abut a nose of the avalanche victim 20 and assure further sealing of the face mask member 154 about the nose and chin areas of the avalanche victim 20 to further assist in assuring that the oxygen is utilized entirely by the avalanche victim 20 and does not escape into the surrounding facial area.

The anchor strap assembly 156 is placed about the rear head portion of the avalanche victim 20 and adjusted to fit in a secure manner through use of an anchor buckle member (not shown).

As shown in FIG. 10, the auxiliary power supply assembly 28 includes a battery pack housing 154 enclosing a pair of battery members 156. Each battery member 156 has a positive pole 161 and a negative pole 163.

As shown in FIG. 10, the auxiliary power supply assembly 28 is to provide additional backup power to the oxygen battery member 133 on the oxygen conserving assembly 98 and to a battery member on the radio signal transmit beacon assembly 30 as will be explained.

The radio signal transmit beacon assembly 30 includes an avalanche rescue beacon member 178 having its own power supply through a beacon battery member 180. The avalanche rescue beacon member 178 is known in the prior art and there are numerous, at least four different kinds thereof, which will be discussed.

The radio signal transmit beacon assembly 30 puts out a transmitting radio signal 181 and will be energized to be transmitting subject signals on opening of the closure flap assembly 52 as will be explained in the use and operation of this invention. This will not require any further action of the avalanche victim 20 who may unconscious other than moving the closure flap assembly 52 as will be explained.

The visual location indicator assembly 32 includes a coiled ribbon member 182 having an anchor end 186 secured to an upper inner portion of the intermediate wall 51 of the main pack member 50.

The coiled ribbon member 182 has a free end 188 which is allowed to be discharged when achieving the uncoiled condition indicated at 189 in FIG. 13. The coiled ribbon member 182 is dispensed in hopes of leaving a visual indication of a portion of the uncoiled ribbon member 189 above the packed snow after an avalanche and burying of the avalanche victim 20.

As noted in FIG. 13, the uncoiled ribbon member 189 has direction indicia 184 thereon and, more particularly, a pointed arrow indicia 190 which will allow the avalanche rescuers 21 to know which way to proceed to find the avalanche victim 20 in case only a mid portion of the uncoiled ribbon member 189 is exposed above the top surface of the avalanche snow pack.

As noted in FIG. 5A, the coiled ribbon member 182 rests on the ribbon support strap 61 and, after the closure flap member 62 is moved to the opened condition about the closure hinge member 64, the coiled ribbon member 182 rolls outwardly therefrom under the force of gravity in a natural manner when the avalanche victim 20 is caught in the initial stages of an avalanche as noted in FIG. 11. Hopefully, the free end 188 of the coiled ribbon member 182 will trail outwardly behind the avalanche victim 20 and leave a portion thereof exposed so as to be found by the avalanche rescuers 21 in a manner to be explained.

As noted in FIG. 10, the control circuit assembly 34 includes a pair of battery members 157 within the battery pack housing 155 with each battery member 157 having a positive pole 161 and a negative pole 163.

The positive pole 161 is connected by a line 192 to an automatic "on" switch 194 which automatically provides auxiliary electrical DC current voltage or the oxygen conserving member 134 and the avalanche rescue beacon member 178.

From the automatic "on" switch 194, a line 195 is interconnected to one side of a light bulb 196 in the light assembly 49 to illuminate the light bulb 196 and provide light to a forward portion of the main pack member 50 as noted in FIGS. 3 and 5.

This interior light, in the area in which the avalanche victim 20 has cleared an area with his arms, would provide a measure of comfort and, hopefully, calm the avalanche victim 20 buried in the avalanche snow and, thus, slow down the breathing rate of the avalanche victim 20 so as to be able to calmly survive with the pulsing amount of 95% oxygen for a period of at least one hour or greater.

Different types of radio signal transmit beacon assemblies 30 are known in the prior art and will operate to transmit or receive radio signals therefrom. The applicant's radio signal transmit beacon assembly 30 will automatically switch to transmitting radio signals 181 so as to be picked up by a radio signal transmit beacon assembly 30 in a receiving mode by the avalanche rescuers 21 in order to locate the buried avalanche victim 20.

Numerous ones are known in the prior art as avalanche transceivers, one being a tracker DTS (Digital Transceiving System), utilizing smart DTS technology creates significant faster rescues and is simple to learn how to operate.

Another type of avalanche rescue beacon is known as an Ortovox Model M1 avalanche rescue beacon. This beacon has an excellent track record in avalanche rescue and is curved to fit comfortably against the body of the avalanche victim 20.

One further type of avalanche rescue beacon is the Orotvox Model F1 Focus avalanche rescue beacon and is very popular among ski patrols around the world.

Still, another type of avalanche rescue beacon is the Pieps Opti-4 avalanche rescue beacon which has features showing increasing radio signals when it is transmitting a radio beacon signal. This unit also has a greater number of sensitivity or distance setting so as to more readily find the avalanche victim 20 by the avalanche rescuers 21.

It is important that the CO2 be naturally displaced from the avalanche victim 20 during a normal breathing operation and not allowed to condense so as to be re-input or recycled after discharge by the avalanche victim 20. This dispensing of CO2 can be achieved through the applicant's use of the CO2 absorbing foam materials 58 contained within the main pack member 50 and, more specifically, between the back wall 49 and the intermediate wall 51 as noted in FIG. 5A. This area can be filled with calcium oxide or calcium hydroxide, being a soda lime, which also contains an activated carbon or activated carbon fabric to absorb the CO2.

One known material is an activated carbon fabric manufactured by "Kothmex" and is unique as it has an enormous absorption capacity but incredible high speed absorption.

The Kothmex activated carbon fabric is manufactured by Taiwan Carbon Technology Company, LTD at Taichung, Taiwan, ROC.

It is also known in the prior art that numerous types of CO2 absorbent canisters are available using soda lime therein to absorb the CO2.

The CO2 absorbing foam material 58 operates as a shock absorber protecting the avalanche victim 20 when tumbling head over heels during movement down a mountain during an active avalanche movement condition.

The avalanche survival pack assembly of this invention is economical to manufacture; sturdy in construction, reliable in operation; compact in nature to be worn against a chest area of a cross country or downhill skier or other user; automatic in operation; and substantially maintenance free.

It is to be noted that the avalanche survival pack assembly has numerous applications as previously noted such as downhill skiers, cross country skiers, helicopter skiers, snow shoers, cat or snow plow operators, helicopter guides, back country guides, snow safety professionals, and back country skiers.

USE AND OPERATION OF THE INVENTION

In the use and operation of the invention, the avalanche survival pack assembly 12 is first checked to make sure that the oxygen cylinder members 104 are filled to capacity under 3000 pounds PSI. At this time, the pressure gauge member 130 is to be checked to ascertain whether or not the outgoing pressure from the pressure regulator member 124 is at a desirable range of 20 PSI.

Next, the auxiliary power supply assembly 28 would be checked to ascertain whether the batteries are fully charged therein. A push button would be depressed and an indicator light 210 (FIG. 2) would show the status of subject batery members 156.

A check would be completed to make sure that the nose/mouth mask assembly 102 is present therein and properly connected to the oxygen conserving assembly 98.

Next, the cross country or downhill skier 14 or other user would mount the main support chest pack assembly 24 about the waist and shoulder areas with use respectively of the waist support assembly 46 and the shoulder harness assembly 48.

The respective snap lock belt buckle members (not shown) would be utilized to firmly clamp about the waist and shoulder areas of the user thereof with the main pack assembly 36 pressed against the chest area of the user thereof.

The user would check the power indicator light 210 on the auxiliary power supply assembly 28 to ascertain that it was fully charged. An additional power indicator light 212 on the radio signal transmit beacon assembly 30 would be checked to indicate that the battery 180 is active and charged.

A push button test member could be utilized to momentary indicate whether the light bulb 196 is working.

Next, on approaching an avalanche prone ski area, the cross country or downhill skier 14 or user thereof would activate the radio signal transmit beacon assembly 30 to the transmit condition. However, the avalanche survival pack assembly 12 of this invention is provided with the automatic "on" switch 194 so that, if the user thereof forgets to place in a transmit condition, the radio signal transmit beacon assembly 30 will automatically be activated to the "send" signal transmit condition on being energized from the auxiliary power supply assembly 28 in a manner well known in the prior art.

On proceeding in the avalanche prone area, the cross country or downhill skier 14 or other user thereof may find themselves under the threat of an avalanche which, in an active condition, is signaled by a loud, cracking noise or a "whoomph" sound. In this situation, the potential avalanche victim 20 must instantly evaluate its chances of getting out of the path of the rumbling avalanche condition. This condition will normally be instantly obvious to the avalanche victim 20 and, if escape is not possible, the potential avalanche victim 20 must take immediate action as follow:

1) rip the closure flap assembly 52 to the forward open condition by pulling on the detach ring members 68 outwardly;
2) then immediately pull the nose/mouth mask assembly 102 outwardly and place it on its head portion, namely, placing the anchor strap assembly 156 about the user's head portion and placing the teeth grip member 170 within the users mouth and clamp down thereupon;
3) kick the skis 16 off while disposing of the ski poles 18 and start to "swim" with the approaching or co-mingling avalanche snow and debris and "swimming" to stay on top thereof if possible;
4) as the speed and flow of the avalanche material starts to slow down, the user fights to stay on a top surface, or as close to the top as possible;

5) at the last few seconds before the avalanche flow completely stops, the user must utilize its arms and push the snow away from the user's face to create a cavity in front of the face and chest areas as large as possible and, if the snow sets, the user's hands should be up around the face and chest area; and 6) above the top surface of the avalanche snow and debris, hopefully the avalanche rescuers 21 will proceed on searching for the avalanche victim 20 utilizing their radio signal transmit beacon assembly 30 which would be set in the "receive" condition.

Further, the avalanche rescuers 21 may be able to observe a portion of the visual location indicator assembly 32 and, namely, the free end 188 of the uncoiled ribbon member 189. If this is observable, the direction indicia 184 with the arrow indicia 190 will indicate to the avalanche rescuers 21 which way to follow the uncoiled ribbon member 189 which then leads to the location of the avalanche victim 20.

As noted in FIG. 12, the avalanche rescuers 21 are on a top surface of the avalanche snow pack and have available thereto the location of the avalanche victim 20 through the transmitting radio signal 181; their own radio signal transmit beacon assembly 30 set to a "receive" condition to receive the transmitting radio signals 181; visual observation of a portion of the visual location indicator assembly 32; and use of the high strength probing rods 214 that are used to find location of the avalanche victim 20.

The oxygen supply reservoir assembly 90 with the oxygen cylinder members 104 having 95% oxygen therein at 3000 pounds PSI will supply oxygen through the oxygen conserving assembly 98 at a predetermined pulsating setting in order to provide an hour or more of life-sustaining oxygen to the avalanche victim 20 which will greatly increase its chances for survival.

The light assembly 49 provides a soothing and comforting affect light to the area in front of the avalanche victim 20 so as not to increase the pulse rate of the avalanche victim 20 and, thus, allow less oxygen from the oxygen conserving assembly 98 to comfortably sustain life of the avalanche victim 20 until rescued.

While the invention has been described in conjunction with preferred specific embodiments thereof, it will be understood that this description is intended to illustrate and not to limit the scope of the invention, which is defined by the following claims.

I claim:

1. An avalanche survival pack assembly to be worn by a user comprising:

a) a main support chest pack assembly connected to the user thereof;

b) an oxygen supply means including an oxygen conserving assembly operable on activation to deliver a controlled amount of oxygen in a pulsating mode to the user after becoming an avalanche victim;

c) a radio signal transmit beacon assembly to emit a transmitting radio signal from the main support chest pack assembly to signal location of the avalanche victim;

d) a visual location indicator assembly having a ribbon member dispensed from said main support chest pack assembly on the user becoming a potential avalanche victim; and e) said visual location indicator assembly having an indicator indicia on said ribbon member to indicate which direction said main support chest pack assembly is located with the user attached thereto;

whereby said transmitting radio signal can be traced to the avalanche victim by rescuers using a radio transceiver assembly; said oxygen supply means can transfer life-sustaining oxygen to the avalanche victim for at least a period of one hour; and a portion of said ribbon member should be above a top surface of the avalanche snow pack to be observed by the avalanche rescuers.

2. An avalanche survival pack assembly, comprising:

a) a main support assembly to be worn and connected adjacent a chest area by a user thereof;

b) an oxygen supply means conveyed in said main support assembly;

c) said oxygen supply means includes an oxygen supply reservoir to supply high pressure oxygen through a pressure regulator assembly which supplies low pressure oxygen to a nose/mouth mask assembly to be worn by an immediately potential avalanche victim;

d) a visual location indicator assembly having an elongated signal member dispensed from said main support assembly just prior to becoming an avalanche victim;

e) said signal member having indicator indicia to indicate direction to follow so as to be traced back to the main support assembly and, thus, the avalanche victim; and f) means to automatically energize said oxygen supply means and dispense said signal member when the user encounters avalanche emerging conditions.

3. An avalanche survival pack assembly as described in claim 2, wherein:

a) said oxygen supply means including an oxygen conserving assembly attached to a high pressure output from said oxygen supply reservoir assembly and a low pressure output from high pressure oxygen through a pressure regulator member which supplies low pressure oxygen in a pulsating mode to said nose/mouth mask assembly in a predetermined amount to sustain life to the avalanche victim.

4. An avalanche survival pack assembly as described in claim 2, wherein:

a) said nose/mouth mask assembly provided with a one-way valve assembly whereupon discharged air from the avalanche victim moves through the one-way valve assembly so that only oxygen is taken in by the avalanche victim.

5. An avalanche survival pack assembly as described in claim 2, comprising:

a) said main support assembly includes a main pack assembly having a main pack member with a closure flap assembly;

b) said closure flap assembly movable to an actuated condition on the user encountering an avalanche flow condition to automatically energize said oxygen supply means, said visual location indicator assembly and a radio signal transmit beacon assembly whereby said oxygen supply means supplies oxygen to the avalanche victim through said nose/mouth mask assembly; and c) said visual location indicator assembly is dispensed from said main support assembly to provide the elongated signal member and said radio signal transmit beacon assembly is energized to transmit a transmitting radio signal to avalanche rescuers.

6. An avalanche survival pack assembly as described in claim 5, wherein:

a) said signal member having arrow indicia pointing to said main support assembly worn by the user to assist the avalanche rescuers in saving the life of subject user.

7. An avalanche survival pack assembly as described in claim 2, wherein:

a) said main support means includes a light assembly operable to be energized to illuminate an area in front of the avalanche victim.

8. An avalanche survival pack assembly as described in claim 2, wherein:

a) said main support chest pack assembly includes a CO2 absorbing member to receive and absorb carbon dixoide thereabout.

9. An avalanche survival pack assembly, comprising:

a) a main support assembly to be worn and connected adjacent a chest area by a user thereof;

b) an oxygen supply means conveyed in said main support assembly;

c) said oxygen supply means includes an oxygen supply reservoir to supply high pressure oxygen through a pressure regulator assembly which supplies low pressure oxygen to a nose/mouth mask assembly to be worn by an immediately potential avalanche victim;

d) a visual location indicator assembly having an elongated signal member dispensed from said main support assembly just prior to becoming an avalanche victim;

e) said signal member can be traced back to the main support assembly and, thus, the avalanche victim;

f) means to automatically energize said oxygen supply means and dispense said signal member when the user encounters avalanche emerging conditions;

g) said main support assembly includes a main pack assembly having a main pack member with a closure flap assembly;

h) said closure flap assembly movable to an actuated condition on the user encountering an avalanche flow condition to automatically energize said oxygen supply means, said visual location indicator assembly and a radio signal transmit beacon assembly whereby said oxygen supply means supplies oxygen to the avalanche victim through said nose/mouth mask assembly;

i) said visual location indicator assembly is dispensed from said main support assembly to provide said elongated signal member and said radio signal transmit beacon assembly is energized to transmit transmitting radio signal to avalanche rescuers; and j) movement of said closure flap assembly operates to energize a light assembly to illuminate an area in front of the avalanche victim and closes an "on" switch to automatically energize said oxygen supply means and a radio signal transmit beacon assembly.

10. An avalanche survival pack assembly to be worn by a user normally in adverse weather conditions, comprising:

a) a main support means which includes a main pack assembly to receive and support elements on a user thereof;

b) an oxygen supply means mounted on said main support means operable to supply oxygen to the user through a mask assembly;

c) a radio signal transmit beacon assembly mounted on said main support means operable to emit a radio signal from said main support means to pin point location of an avalanche victim;

d) a visual location indicator assembly including a coiled ribbon member having directional indicia thereon secured at one end to said main support means; and e) means to energize and operate an auxiliary power supply assembly and said oxygen supply means, activate said radio signal transmit beacon assembly to emit the radio signal, and release said coiled ribbon member into an uncoiled ribbon member trailing said main support means just prior to the user becoming an avalanche victim.

11. An avalanche survival pack assembly as described in claim 10, including:

a) a main support means having a plurality of support pocket members to individually receive and support elements being an accessory pocket assembly, a battery pack pocket assembly, a filler valve pocket assembly, and a radio beacon pocket assembly;

b) said means to energize includes an automatic "on" switch closed when a portion of said main support means is moved to an open position and operable to energize said oxygen supply means; said radio signal transmit beacon assembly; and said visual location indicator assembly so as to provide means to find location of the avalanche victim by avalanche rescuers.

12. An avalanche survival pack assembly as described in claim 10, wherein:

a) said oxygen supply means includes an oxygen supply reservoir assembly to provide high pressure oxygen to a pressure regulator assembly which supplies low pressure oxygen to an oxygen conserving assembly; and b) said oxygen conserving assembly provides pulses of oxygen to said mask assembly to sustain life in the avalanche victim for at least one hour.

13. An avalanche survival pack assembly as described in claim 12, wherein:

a) said mask assembly includes a one-way valve operable to exhaust exhaled air with CO2 therein away from the avalanche victim; and b) a nose strap member of a deformable material to be depressed to achieve a seal against the user's nose to prevent loss of oxygen about the mask assembly.

14. An avalanche survival pack assembly, comprising:

a) a main support chest pack assembly connected to the user thereof;

b) an oxygen supply means including an oxygen conserving assembly operable on activation to deliver a controlled amount of oxygen in a pulsating mode to the user after becoming an avalanche victim;

c) a radio signal transmit beacon assembly to emit a transmitting radio signal from the main support chest pack assembly to signal location of the avalanche victim;

d) a visual location indicator assembly having a ribbon member dispensed from said main support chest pack assembly on the user becoming a potential avalanche victim; and e) said main support means includes a light assembly operable to be energized to illuminate an area in front of the avalanche victim;

whereby said transmitting radio signal can be traced to the avalanche victim by rescuers using a radio transceiver assembly; said oxygen supply means can transfer life-sustaining oxygen to the avalanche victim for at least a period of one hour; and a portion of said ribbon member should be above a top surface of the avalanche snow pack to be observed by the avalanche rescuers.

* * * * *